United States Patent
Su et al.

(10) Patent No.: US 9,958,262 B2
(45) Date of Patent: May 1, 2018

(54) SYSTEM FOR MEASURING THREE-DIMENSIONAL PROFILE OF TRANSPARENT OBJECT OR REFRACTIVE INDEX BY FRINGE PROJECTION

(71) Applicant: National Sun Yat-sen University, Kaohsiung (TW)

(72) Inventors: Wei-Hung Su, Kaohsiung (TW); Chau-Jern Cheng, Kaohsiung (TW); Guang-Hong Chen, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 371 days.

(21) Appl. No.: 14/833,174

(22) Filed: Aug. 24, 2015

(65) Prior Publication Data

US 2016/0238381 A1     Aug. 18, 2016

(30) Foreign Application Priority Data

Feb. 17, 2015  (TW) .............................. 104105692 A

(51) Int. Cl.
  *G01B 11/25*  (2006.01)
  *G01N 21/958*  (2006.01)

(52) U.S. Cl.
  CPC .......... *G01B 11/25* (2013.01); *G01B 11/2531* (2013.01); *G01N 21/958* (2013.01)

(58) Field of Classification Search
  CPC ................ G01B 11/25; G01B 11/2522; G01N 2021/9586; G01M 11/025
  See application file for complete search history.

(56) References Cited

U.S. PATENT DOCUMENTS

| | | | |
|---|---|---|---|
| 6,438,272 B1 | 8/2002 | Huang et al. | |
| 8,224,064 B1 | 7/2012 | Hassebrook et al. | |
| 8,451,368 B2 | 5/2013 | Sung et al. | |
| 2005/0219522 A1* | 10/2005 | Jones | G01M 11/00 356/239.1 |
| 2013/0301909 A1* | 11/2013 | Sato | G01B 11/25 382/154 |

FOREIGN PATENT DOCUMENTS

| | | | |
|---|---|---|---|
| CN | 102338989 A | 2/2012 | |
| JP | 2003232619 * | 8/2003 | ............ G01B 11/24 |
| TW | 201020512 A1 | 6/2010 | |
| TW | 201109735 A1 | 3/2011 | |

OTHER PUBLICATIONS

Wei-Hung Su, Chau-Jern Cheng, and Yi-Ta Lee. 3D shape measurements for plano-convex lenses using fringe projection techniques. Sep. 5, 2014, SPIE Proceedings vol. 9200.

* cited by examiner

*Primary Examiner* — Tri Ton
*Assistant Examiner* — Rebecca C Bryant
(74) *Attorney, Agent, or Firm* — Soroker Agmon Nordman

(57) ABSTRACT

A system for measuring the profile or the refractive index of a transparent object by fringe projection techniques is provided and has an image generating device, an image capture device, and an image processor. The image generating device produces a reference image with a long depth of focus. This reference image is emitted into an inspected transparent object, and is distorted by the refractive index and the profile of the transparent object. The image capture device receives the distorted image. The image processor analyzes the difference between the distorted image and the reference image, so as to identify the profile or the refractive index of the inspected transparent object.

16 Claims, 4 Drawing Sheets

SYSTEM FOR MEASURING THREE-DIMENSIONAL PROFILE OF TRANSPARENT OBJECT OR REFRACTIVE INDEX BY FRINGE PROJECTION

CROSS REFERENCE TO RELATED APPLICATIONS

This application claims the priority of Taiwan Patent Application No. 104105692, filed on Feb. 17, 2015. This invention is partly disclosed in a thesis entitled "3D shape measurements for plano-convex lenses using fringe projection techniques" on Sep. 5, 2014 completed by Wei-Hung Su.

FIELD OF THE INVENTION

The present invention relates to a system for measuring a transparent object, and more particularly to a system for measuring a transparent object by fringe projection.

BACKGROUND OF THE INVENTION

In the prior art, a general fringe projection profilometry can measure the 3D shape/profile of a non-transparent object. In addition, an interferometer can measure the thickness or a refractive index of the transparent object, but the measurement must be executed in a noise-isolated, vibration-free, and stable environment. If the surface has faults or flaws, the result will be false positives on the shape measurement.

Therefore, it is necessary to provide a system for measuring a transparent object by fringe projection to solve the above described problems.

SUMMARY OF THE INVENTION

A primary object of the present invention is to provide a system for measuring a transparent object by fringe projection, which projects a fringe pattern having a sinusoidal distribution penetration ratio onto a transparent object. After the fringe pattern penetrates the transparent object, an image capture device records a distorted image distribution, and the image processor analyzes the distorted image to identify the profile of the inspected transparent object or the corresponding refractive index.

To achieve the above object, the present invention provides a system for measuring a transparent object by fringe projection, which is used to form the profile of an inspected transparent object, and the system comprises: a long depth of focus (DOF) image generating device, an image capture device, and an image processor. The DOF image generating device generates a long DOF image, and the long DOF image is emitted into the inspected transparent object; the image capture device receives a distorted image which is generated by the long DOF image emitted into the inspected transparent object and then refracted therefrom; and the image processor is electrically connected to the image capture device, wherein the image processor pre-stores the long DOF image, wherein the image processor analyzes the distorted image and compares the distorted image with the long DOF image, so as to identify the profile of the inspected transparent object or the corresponding refractive index.

In one embodiment of the present invention, the long DOF image is generated from a fringe image which has a sinusoidal distribution penetration ration when the long DOF image is emitted into the inspected transparent object.

In one embodiment of the present invention, the fringe image has fringes arranged based on a greyscale encoding, which is used to measure the multi-sectional shape of the complex transparent objects, or to simultaneously measure several transparent objects randomly scattered in one space.

In one embodiment of the present invention, the long DOF image generating device comprises: a two-dimensional amplitude grating, a light source, and a wide-angle lens. The light source illuminates the two-dimensional amplitude grating, so as to generate a two-dimensional fringe image; and the wide-angle lens receives the two-dimensional fringe image passing therethrough and generating the long DOF image.

In one embodiment of the present invention, the long DOF image generating device comprises: a two-dimensional amplitude grating, a point light source, and a convex lens. The point light source illuminates the two-dimensional amplitude grating, so as to generate a two-dimensional fringe image; and the convex lens receives the two-dimensional fringe image passing therethrough and generates the long DOF image.

In one embodiment of the present invention, the two-dimensional amplitude grating is a two-dimensional pattern hologram.

In one embodiment of the present invention, the long DOF image generating device comprises: a Young's double slit, a laser light source, and a convex lens. The laser light source emits a laser light into the Young's double slit and generates a one-dimensional fringe image which has a sinusoidal distribution penetration ratio; and the convex lens adjusts a magnification and a divergence angle of the one-dimensional fringe image passing through the convex lens, so as to generate the long DOF image.

In one embodiment of the present invention, the system further comprises: a moving mechanism moving the inspected transparent object so as to measure the profile of different parts of the inspected transparent object; or the system further comprises a rotation mechanism rotating the inspected transparent object along a clockwise direction or a counterclockwise direction, so as to detect the distorted images which are generated by the long DOF image emitted into the inspected transparent object at different angels and then analyze the profile or an index of refraction of the inspected transparent object.

In one embodiment of the present invention, the system further comprises a moving screen disposed between the inspected transparent object and the image capture device, wherein the distorted image of the inspected transparent object is projected onto the moving screen firstly, and then the image capture device receives the distorted image on the moving screen.

In one embodiment of the present invention, the image capture device is a charge-coupled device (CCD) camera.

In summary, a system for measuring a transparent object by fringe projection effectively detects the image which is caused by fringes projected onto the inspected transparent object. The present invention has a simple structure and high stability. The present invention is adapted for an environment with noises and vibrations, and also adapted for the shape measurement of great-size objects. The measuring principle of the present invention is projecting a DOF image having a sinusoidal distribution penetration ratio passing through the inspected transparent object, the image capture device then records the fringe distribution after the DOF image penetrates the inspected transparent object. The refractive index of the transparent object is different from the air, after the DOF image penetrates the inspected transparent object, the emitting direction will be changed. The image capture device obtains a distorted fringe image, and the distortion degree of the distorted fringe image is related to the shape, thickness, and the refractive index of the inspected transparent object. The image processor analyzes the distorted image to identify the profile of the inspected transparent object, or the corresponding refractive index. In the present invention, the system for measuring a transparent object by fringe projection is adapted for a variety of the optical detection, such as the shape measurement of a lens in the optical industry, the shape analysis of biological cells in medical engineering, the shape of optical fibers in the telecommunication industry, and breaking points identification.

DETAILED DESCRIPTION OF THE PREFERRED EMBODIMENTS

The structure and the technical means adopted by the present invention to achieve the above and other objects can be best understood by referring to the following detailed description of the preferred embodiments and the accompanying drawings. Furthermore, directional terms described by the present invention, such as upper, lower, front, back, left, right, inner, outer, side, longitudinal/vertical, transverse/horizontal, etc., are only directions by referring to the accompanying drawings, and thus the used directional terms are used to describe and understand the present invention, but the present invention is not limited thereto.

Figure 1:
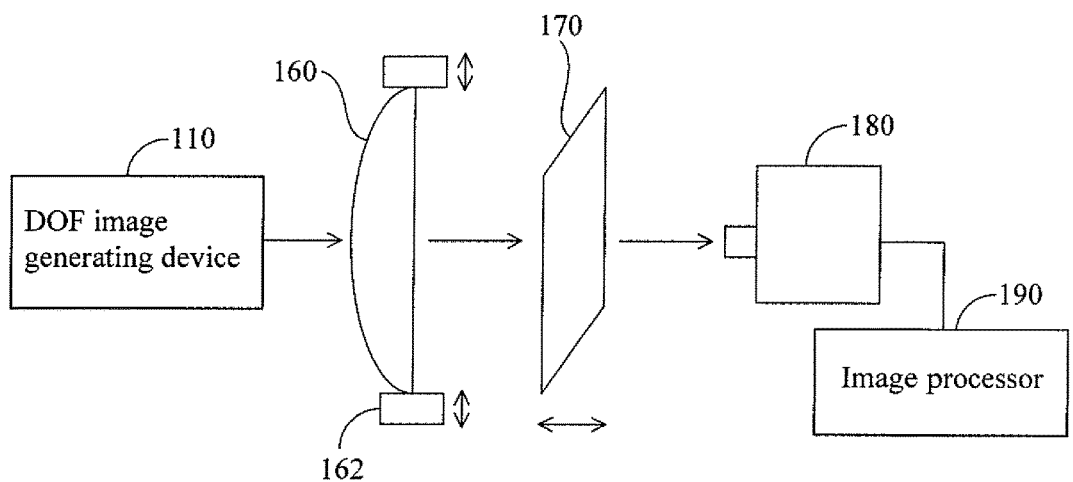
FIG. 1 is a diagram of a system for measuring the shape or refractive index of a transparent object by fringe projection according to a first embodiment of the present invention.

Refer to FIG. 1, which is a diagram of a system for measuring the shape or refractive index of a transparent object by fringe projection according to a first embodiment of the present invention. The system comprises a DOF image generating device 110, a moving mechanism 162, a moving screen 170, an image capture device 180, and an image processor 190, and the system is used to measure the shape of the inspected transparent object 160. In the first embodiment, the inspected transparent object 160 can be a plano-convex lens, but is not limited thereto. The moving mechanism 162 is used to move the inspected transparent object 160, so as to measure the shape of each part of the inspected transparent object 160. The moving mechanism 162 also can be a rotation mechanism which is used to rotate the inspected transparent object 160 along a clockwise direction or a counter clockwise direction, so as to effectively detect the distorted image with different emitting angles. As a result, the system of the present invention has enough parameters, so as to analyze the shape or the refractive index of the inspected transparent object. The moving screen 170 is disposed between the inspected transparent object 160 and the image capture device 180. The image capture device is a charge-coupled device camera, and is used to capture a DOF image generated from the DOF image generating device 110. The image processor 190 is electrically connected to the image capture device 180, and is used to analyze the DOF image captured by the image capture device 180.

Figure 2:
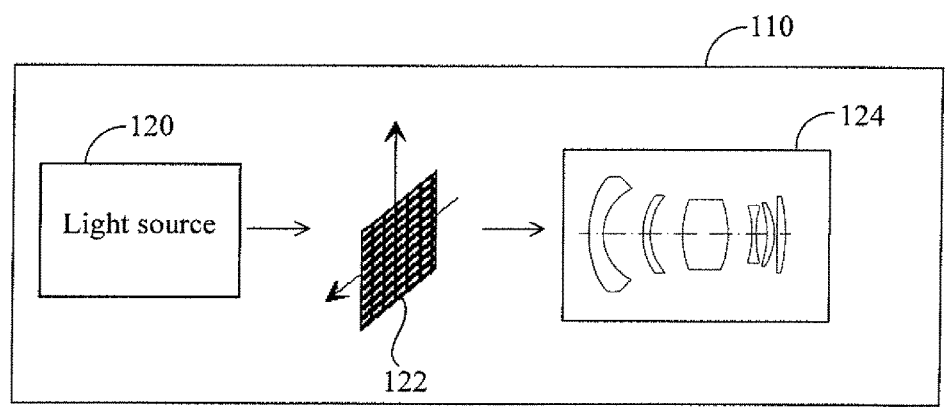
FIG. 2 is a diagram of internal components of a DOF image generating device according to the first embodiment of the present invention.

Refer to FIG. 2, which is a diagram of internal components of a DOF image generating device according to the first embodiment of the present invention. In the first embodiment, the DOF image generating device 110 comprises a light source 120, a two-dimensional amplitude grating 122, and a wide-angle lens 124. The two-dimensional amplitude grating 122 can be a two-dimensional pattern hologram. The light source is used to illuminate the two-dimensional amplitude grating, so as to generate a two-dimensional fringe image. The wide-angle lens receives the two-dimensional fringe image passing therethrough. The wide-angle lens 124 has a lens combination for generating a DOF image. The front lens is a concave lens, and the after lens is a convex lens. The refractive result of the concave lens is different from the convex lens, so as to make the two-dimension fringe image be refracted to a DOF (fringe) image, wherein the DOF image has a sinusoidal distribution penetration ratio. In addition, for the structural design of the two-dimensional amplitude grating 122, the fringe image of the DOF image has a grey scale encoding, so as to effectively avoid misjudging positions of adjacent fringes. Therefore, the present invention contributes in measuring the multi-sectional shape of complex transparent objects, or to simultaneously measuring several transparent objects randomly scattered in one space.

Figure 3:
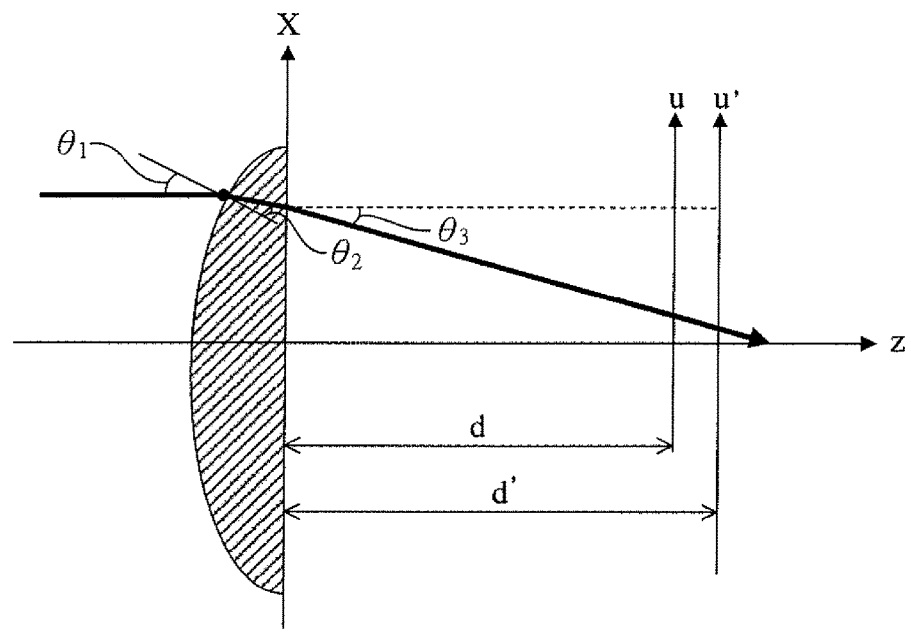
FIG. 3 is a diagram of beam refractions of an inspected transparent object according to the first embodiment of the present invention.

FIG. 3 is a diagram of beam refractions of an inspected transparent object according to the first embodiment of the present invention. The x-axis and the z-axis are coordinate axes corresponding to the inspected transparent object 160. The inspected transparent object is a plano-convex lens, and two sides are a convex side and a flat side respectively. The x axis is set to parallel to the flat side, and the z-axis is set vertical with respect to the x-axis. The u-axis is a reference axis for a disposed first position of the moving screen 170, and the u'-axis is a reference axis for a moved second position of the moving screen 170. The distance between the flat side and the u-axis is d, and the distance between the flat side and the u'-axis is d'.

After the refracting by the wide-angle lens 124, the DOF image is emitted to the inspected transparent object, the incident angle is $\theta_1$. The DOF image firstly passes through the convex side of the inspected transparent object 160 and is refracted from the convex side to generate a refractive angle $\theta_2$. Next, a distorted image passes through the flat side part of the inspected transparent object 160, then refracts from the flat side to generate another refractive angle $\theta_3$. Next, the second-time distorted image of the inspected transparent object 160 is projected onto the moving screen 170 after emission along the refractive angle $\theta_3$, then, the image capture device 180 adjacent to the moving screen 170 receives the second-time distorted image. In addition, the moving screen 170 can be moved from the u-axis to the u'-axis, so as to make the image capture device 180 receive different projection images (fringes with different distortion degrees) when the moving screen 170 is disposed in different positions. The comparisons of multiple projection images are executed, so as to benefit the image processor 190 in evaluating the shape of the inspected transparent object 160. In addition, the moving mechanism 162 moves the inspected transparent object 160 along the x-axis, so as to measure the shape of different parts of the inspected transparent object 160. If the moving mechanism 162 is a rotation mechanism, the rotation mechanism rotates the inspected transparent object 160 according to a reference point which is the intersection of x-axis and z-axis. The rotation mechanism rotates the inspected transparent object 160 along a clockwise direction or a counterclockwise direction, so as to detect the distorted images which are generated by the long DOF image emitted into the inspected transparent object at different angels, and then there are enough parameters to analyze the profile or an index of refraction of the inspected transparent object 160.

The image processor 190 is electrically connected to the image capture device 180. The image processor 190 is used to pre-store the DOF image. The image processor 190 analyzes the distorted image and compares the distorted image and the DOF image to identify the shape of the inspected transparent object 160. In the DOF image of the present invention, any N fringes are not repeated; in other words, any N fringes are unique in the DOF image. After the refraction of the inspected transparent object 160, the image processor 190 still can find the unique N fringes of the distorted image which is captured by the image capture device 180. Accordingly, the image processor 190 analyzes an "A" image block, wherein the "A" image block is a set of a plurality of fringes. After being refracting from the inspected transparent object, the "A" image block is distorted into a "B" image block. The image processor 190 compares the "A" image block to the "B" image block, and the image processor 190 identifies the shape, a thickness, and a refractive index of a "C" area which the "A" image block projected onto the inspected transparent object 160 according to the distortion degree. The moving mechanism 162 moves or rotates the inspected transparent object 160 many times, so as to make the image capture device 180 capture the shape of different parts of the inspected transparent object 160. The moving mechanism 162 moves the moving screen 170, for example, moving from the u-axis to the u'-axis, so as to make the image capture device 180 capture projection images with different depths (fringes with different distortion degrees) when the moving screen 170 is disposed in different positions. Therefore, the image processor 190 analyzes multiple distorted images and compares the distorted images to the DOF image, so as to identify the overall shape and thickness of the inspected transparent object 160.

Figure 4:
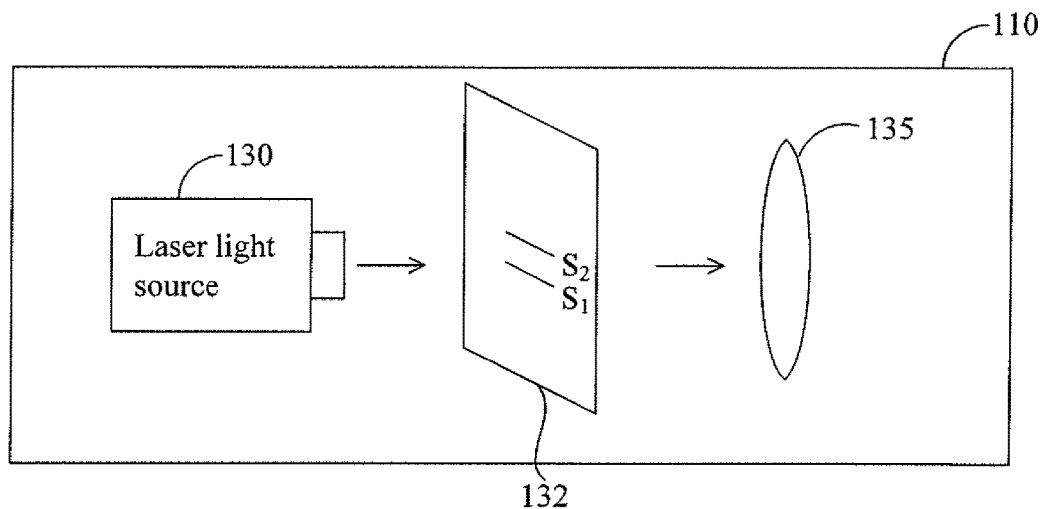
FIG. 4 is a diagram of internal components of a DOF image generating device according to a second embodiment of the present invention.
Figure 5:
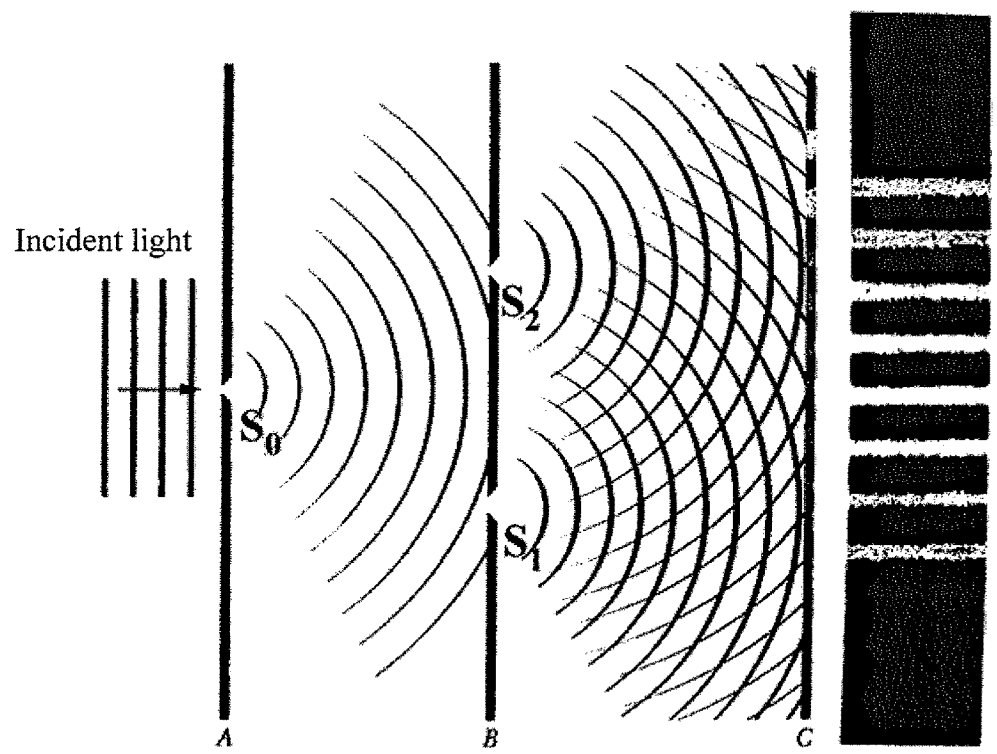
FIG. 5 is a diagram of an interference of a Young's double slit according to the second embodiment of the present invention.

FIG. 4 is a diagram of internal components of a DOF image generating device according to a second embodiment of the present invention. In the second embodiment, the DOF image generating device 110 comprises a laser light source 130, a Young's double slit 132 and a convex lens 135. The laser light source 130 emits a laser light into the Young's double slit 132, and the Young's double slit interference is as illustrated in FIG. 5. The laser light signal emitting by the laser light source 130, which has the same result as a general parallel incident light passes through a slit S0. Next, the laser light signal passes a slit S1 and a slit S2 so as to generate an interference, and then a DOF image is generated. The DOF image is a one-dimensional fringe image which has a sinusoidal distribution penetration ratio. The convex lens 135 is used to adjusting a magnification and a divergence angle of the one-dimensional fringe image.

Figure 6:
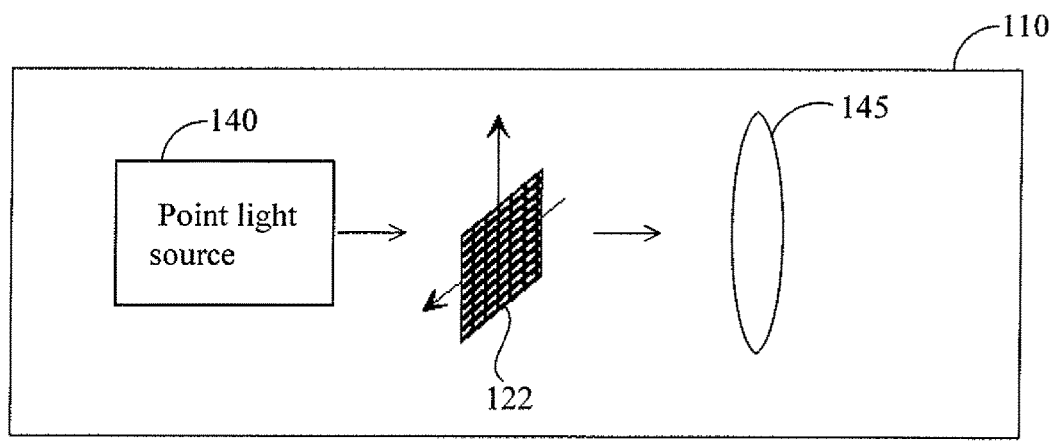
FIG. 6 is a diagram of internal components of a DOF image generating device according to a third embodiment of the present invention.

FIG. 6 is a diagram of internal components of a DOF image generating device according to a third embodiment of the present invention. In the third embodiment of the present invention, the DOF image generating device 110 comprises: a point light source 140, a two-dimensional amplitude grating 233 and a convex lens 145. The point light source 140 illuminates the two-dimensional amplitude grating 122, so as to generate a two-dimensional fringe image. The convex lens 145 is used to receive the two-dimensional fringe image passing therethrough and generate the long DOF image. The third embodiment also generates a DOF fringe image which is the same as the first embodiment through replacing some components. In addition, in other embodiments of the present invention, the DOF image generating device 110 comprises a laser light source, a diffraction grating, and a convex lens, which is used to generate a DOF image. By executing the above components, the DOF fringe image the same as in the first embodiment is also generated.

In summary, a system for measuring a transparent object by fringe projection is effective in detecting the image which is caused by fringes projected onto the inspected transparent object. The present invention has a simple structure and high stability. The present invention is adapted for an environment with noises and vibrations, and also adapted for the shape measurement of great-size objects The measuring principle of the present invention is projecting a DOF image having a sinusoidal distribution penetration ratio onto the inspected transparent, the image capture device then records the fringe distribution after the DOF image penetrates the inspected transparent object. The refractive index of the transparent object is different from the air, and after the DOF image penetrating the inspected transparent object, the emitting direction will be changed. The image capture device obtains a distorted fringe image, and the distortion degree of the distorted fringe image is related to the shape, thickness, and the refractive index of the inspected transparent object. The image capture device captures projection images with different depths of filed (fringes with different distortion degrees). The image processor analyzes the distorted image and compares the distorted image with the long DOF image, so as to identify the profile of the inspected transparent object or the refractive index. In the present invention, the system for measuring a transparent object by fringe projection is adapted for a variety of optical detections, such as the shape measurement of a lens in the optical industry, the shape analysis of biological cells in medical engineering, the shape of optical fibers in the telecommunication industry, and breaking points identification.

The present invention has been disclosed with preferred embodiments thereof, but the above described preferred embodiments are not intended to limit the present invention. Those who are skilled in the art can make many changes and modifications to the described embodiment which can be carried out without departing from the scope and the spirit of the invention that is intended to be limited only by the appended claims.

What is claimed is:

1. A system for measuring a transparent object by fringe projection, measuring a profile or refractive index of an inspected transparent object, the system comprising:
   a long depth of focus (DO) image generating device configured to generate a long DOF image,
   wherein the long DOF image is emitted into the inspected transparent object;
   wherein the long DOF image is generated from a fringe image which has a sinusoidal distribution penetration ratio when the long DOF image is emitted into the inspected transparent object; and wherein the long DOF image generating device comprises:
- a two-dimensional amplitude grating;
- a light source configured to illuminate the two-dimensional amplitude grating, to generate a two-dimensional fringe image; and
- a wide-angle lens configured to receive the two-dimensional fringe image passing therethrough and generate the long DOF image;

an image, capture device configured to receive a distorted image which is generated by the long DOF image emitted into the inspected transparent object and then refracted by the inspected transparent object; and an image processor electrically connected to the image capture device, wherein the image processor pre-stores the long DOF image, wherein the image processor analyzes the distorted image and compares the distorted image with the long DOF image, to identify the profile or refractive index of the inspected transparent object.

2. The system for measuring a transparent object by fringe projection according to claim 1, wherein the fringe image has fringes arranged based on a greyscale encoding.

3. The system for measuring a transparent object by fringe projection according to claim 1, wherein the two-dimensional amplitude grating is a two-dimensional pattern hologram.

4. The system for measuring a transparent object by fringe projection according to claim 1, wherein the system further comprises: a moving mechanism configured to move the inspected transparent object, to measure the profile or refractive index of different parts of the inspected transparent object; or the system further comprises a rotation mechanism configured to rotate the inspected transparent object along a clockwise direction or a counterclockwise direction, to detect the distorted images which are generated by the long DOF image emitted into the inspected transparent object at different angels and then analyze the profile or an index of refraction of the inspected transparent object.

5. The system for measuring a transparent object by fringe projection according to claim 1, wherein the system further comprises a moving screen disposed between the inspected transparent object and the image capture device, wherein the distorted image of the inspected transparent object is projected onto the moving screen firstly, and then the image capture device receives the distorted image on the moving screen.

6. The system for measuring a transparent object by fringe projection according to claim 1, wherein the image capture device is a charge-coupled device (CCD) camera.

7. A system for measuring a transparent object by fringe projection, measuring a profile or refractive index of an inspected transparent object, the system comprising:
- a long depth of focus (DOF) image generating device configured to generate a long DOF image,
- wherein the long DO image is emitted into the inspected transparent object;
- wherein the long DOF image is generated from a fringe image which has a sinusoidal distribution penetration ratio when the long DOF image is emitted into the inspected transparent object; and
- wherein the long DOF image generating device comprises:
  - a two-dimensional amplitude grating;
  - a point light source configured to illuminate the two-dimensional amplitude grating, to generate a two-dimensional fringe image; and
  - a convex lens configured to receive the two-dimensional fringe image passing therethrough and generate the long DOF image;

an image capture device configured to receive a distorted image which is generated by the long DOF image emitted into the inspected transparent object and then refracted by the inspected transparent object; and an image processor electrically connected to the image capture device, wherein the image processor pre-stores the long DOF image, wherein the image processor analyzes the distorted image and compares the distorted image with the long DOF image, to identify the profile or refractive index of the inspected transparent object.

8. The system for measuring a transparent object by fringe projection according to claim 7, wherein the two-dimensional amplitude grating is a two-dimensional pattern hologram.

9. The system for measuring a transparent object by fringe projection according to claim 7, wherein the fringe image has fringes arranged based on a grey scale encoding.

10. The system for measuring a transparent object by fringe projection according to claim 7, wherein the system further comprises: a moving mechanism configured to move the inspected transparent object, to measure the profile or refractive index of different parts of the inspected transparent object; or the system further comprises a rotation mechanism configured to rotate the inspected transparent object along a clockwise direction or a counterclockwise direction, to detect the distorted images which are generated by the long DOF image emitted into the inspected transparent object at different angels and then analyze the profile or an index of refraction of the inspected transparent object.

11. The system for measuring a transparent object by fringe projection according to claim 7, wherein the system further comprises a moving screen disposed between the inspected transparent object and the image capture device, wherein the distorted image of the inspected transparent object is projected onto the moving screen firstly, and then the image capture device receives the distorted image on the moving screen.

12. The system for measuring a transparent object by fringe projection according to claim 7, wherein the image capture device is a charge-coupled device (CCD) camera.

13. A system for measuring a transparent object by fringe projection, measuring a profile or refractive index of an inspected transparent object, the system comprising:
- a long depth of focus (DOF) image generating device configured to generate a long DOF image,
- wherein the long DOF image is emitted into the inspected transparent object;
- wherein the long DOF image is generated from a fringe image which has a sinusoidal distribution penetration ratio when the long DOF image is emitted into the inspected transparent object; and
- wherein the long DOF image generating device comprises:
  - a Young's double slit;
  - a laser light source configured to emit a laser light into the Young's double slit and generate a one-dimensional fringe image which has a sinusoidal distribution penetration ratio; and a convex lens configured to adjust a magnification and a divergence angle of the one-dimensional fringe image passing through the convex lens, to generate the long DOF image;

an image capture device configured to receive a distorted image which is generated by the long DOF image emitted into the inspected transparent object and then refracted by the inspected transparent object; and an image processor electrically connected to the image capture device, wherein the image processor pre-stores the long DOF image, wherein the image processor analyzes the distorted image and compares the distorted image with the long DOF image, to identify the profile or refractive index of the inspected transparent object.

14. The system for measuring a transparent object by fringe projection according to claim 13, wherein the system further comprises; a moving mechanism configured to move the inspected transparent object, to measure the profile or refractive index of different parts of the inspected transparent object; or the system further comprises a rotation, mechanism configured to rotate the inspected transparent object along a clockwise direction or a counterclockwise direction, to detect the distorted images which are generated by the long DOF image emitted into the inspected transparent object at different angels and then analyze the profile or an index of refraction of the inspected transparent object.

15. The system for measuring a transparent object by fringe projection according to claim 13, wherein the system further comprises a moving screen disposed between the inspected transparent object and the image capture device, wherein the distorted image of the inspected transparent object is projected onto the moving screen firstly, and then the image capture device receives the distorted image on the moving screen.

16. The system for measuring a transparent object by fringe projection according to claim 13, wherein the image capture device is a charge-coupled device (CCD) camera.

* * * * *